United States Patent
Drabek

[11] 4,004,031
[45] Jan. 18, 1977

[54] BIS-(O-1-ALKYLTHIO-ETHYLIMINO)-N-METHYL-CARBAMIC ACID)-N,N'-SULPHIDE INSECTICIDES

[75] Inventor: Jozef Drabek, Allschwil, Switzerland

[73] Assignee: Ciba-Geigy Corporation, Ardsley, N.Y.

[22] Filed: July 9, 1975

[21] Appl. No.: 594,381

[30] Foreign Application Priority Data

July 11, 1974 Switzerland .................. 9608/74
May 27, 1975 Switzerland .................. 6749/75

[52] U.S. Cl. .................. 424/327; 260/551 S;
260/566 AC; 424/298; 424/300
[51] Int. Cl.² .................. A01N 9/20
[58] Field of Search .................. 424/298, 300, 327;
260/551 S, 566 AC

[56] References Cited
UNITED STATES PATENTS 3,299,137 1/1967 Payne et al. .................. 260/566
3,506,698 4/1970 Jelinek .................. 260/453

*Primary Examiner*—Leonard Schenkman
*Attorney, Agent, or Firm*—Harry Falber

[57] ABSTRACT

Compounds of the formula I

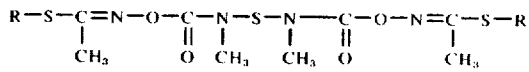

wherein R represents a $C_1$-$C_5$-alkyl radical their manufacture and their use as pest control agents.

13 Claims, No Drawings

BIS-(O-1-ALKYLTHIO-ETHYLIMINO)-N-METHYL-CARBAMIC ACID)-N,N'-SULPHIDE INSECTICIDES

The present invention relates to new bis-(O-1-alkylthio-ethylimino)-N-methylcarbamic acid)-N,N'-sulphides, to processes for their production and to their use in pest control.

This invention relates in particular to bis-(O-1-alkylthio-ethylimino)-N-methylcarbamic acid)-N,N'-sulphides of the formula I

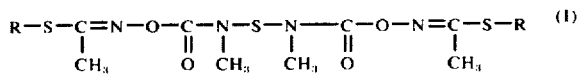

wherein R represents a $C_1$-$C_5$-alkyl radical.

The alkyl radicals denoted by R can be branched-chain or straight-chain. Examples of such radicals are the methyl, ethyl, n-propyl, isopropyl, n-, i-, sec.- and tert.-butyl radical, as well as n-pentyl and isomers thereof.

Compounds of formula I which are preferred on account of their action are those wherein
R represents a methyl, ethyl, n-propyl, isopropyl, n-butyl or i-butyl radical.

The new compounds of the formula I are advantageously obtained by methods known per se; for example, by reacting a compound of the formula II

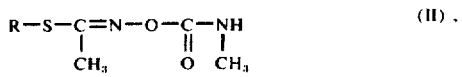

wherein R has the meaning already given under formula I, in the presence of a base, with sulphur chloride ($SCl_2$) or with sulphur monochloride ($S_2Cl_2$).

The process is preferably performed at a reaction temperature of between −10° and 100° C, most preferably between −10° and 30° C, at normal pressure and in the presence of a solvent or diluent inert to the reactants.

Suitable as a base for the process are in particular tertiary amines such as trialkylamines, pyridines and dialkylanilines, also hydroxides, oxides, carbamates and bicarbonates of alkali metals and alkaline-earth metals, as well as alkali metal alcoholates such as potassium-tert.butylate and sodium methylate.

Suitable solvents or diluents are, e.g., ethers and ethereal compounds such as diethyl ether, diisopropyl ether, dioxane or tetrahydrofuran; aliphatic and aromatic hydrocarbons, especially benzene, toluene or xylenes; and ketones such as acetone, methyl ethyl ketone or cyclohexanone.

The starting materials of formula II are themselves already known as insecticides (see the English and U.S. Pat. Nos. 1,138,347 and 3,299,137). The active substances of formula I according to the invention likewise have a very good insecticidal action but are surprisingly, compared with the known compounds of formula II, more species-specific. They are thus suitable in particular for the control of pests on cotton plants and for the control of blue blowflies (Lucilla sericata). Furthermore, the compounds of formula I, compared with the analogues of formula II, such as "Lannate" [$CH_3S$—$C(CH_3)$=N—O—CO—$NHCH_3$], surprisingly have a significantly more favourable toxicity with respect to warm-blooded animals. In addition, they also process nematocidal activity. The insecticidal action of the compounds of the invention can be substantially broadened and adapted to suit given circumstances by the addition of other insecticides. Suitable additives are, e.g.: organic phosphorus compounds, nitrophenols and derivatives thereof, formamidines, ureas, pyrethrin-like derivatives, carbamates or chlorinated hydrocarbons.

The compounds of formula I can be used on their own or together with suitable carriers and/or additives. Suitable carriers and additives may be solid or liquid, and they correspond to the substances common in formulation practice, such as natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice.

The compositions according to the invention are produced in a manner known per se by the intimate mixing and/or grinding of active substances of formula I with suitable carriers, optionally with the addition of dispersing agents or solvents which are inert to the active substances. The active substances can be obtained and used in the following forms:

solid preparations: dusts, scattering agents, granulates, coated granulates, impregnated granulates and homogeneous granulates;

liquid preparations:
a. water-dispersible active-substance concentrates: wettable powders, pastes or emulsions;
b. solutions.

The content of active substance in the described preparations is between 0.1 and 95%.

The active substances of formula I can be formulated, for example, as follows:

Dusts:
The following substances are used in the preparation of (a) a 5% dust, and (b) a 2% dust;
a.
5 parts of active substance, 95 parts of talcum;
b.
2 parts of active substance, 1 part of highly dispersed silicic acid, 97 parts of talcum.

The active substances are mixed and ground with the carriers.

Granulate:
The following substances are used to produce a 5% granulate:
5 parts of active substance,
0.25 part of epichlorohydrin,
0.25 part of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The solution thus obtained is sprayed on to kaolin, and the acetone is subsequently evaporated off in vacuo.

Wettable powder:
The following constituents are used in the preparation of (a) a 40%, (b) and (c) a 25%, and (d) a 10% wettable powder:
a.

40 parts of active substance,
5 parts of sodium lignin sulphonate,
1 part of sodium dibutyl-naphthalene sulphonate,
54 parts of silicic acid;
b.
25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid
19.5 parts of Champagne chalk,
28.1 parts of kaolin;
c.
25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselguhr,
46 parts of kaolin;
d.
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives; the mixture is then ground in the appropriate mills and rollers. Wettable powders are obtained which can be diluted with water to give suspensions of any desired concentration.

Emulsifiable concentrates:

The following substances are used to produce (a) a 10% and (b) a 25% emulsifiable concentrate:
a.
10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;
b.
25 parts of active substance,
2.5 parts of epoxidised vegetable oil,
10 parts of alkylarylsulphonate/fatty alcoholpolyglycol ether mixture,
5 parts of dimethylformamide,
57.5 parts of xylene.

From these concentrates it is possible to prepare, by dilution with water, emulsions of any desired concentration.

Spray:

The following constituents are used to prepare (a) a 5% spray and (b) a 95% spray, respectively:
a.
5 parts of active substance,
1 part of epichlorohydrin,
94 parts of ligroin (boiling limits 160°–190° C); and
b.
95 parts of active substance,
5 parts of epichlorohydrin.

The invention is further illustrated by the following examples:

EXAMPLE 1

Production of bis-[0-(1-methylthioethylimino)-N-methylcarbamic acid]-N,N'-sulphide 32.4 g of 1-(methylthio)-ethylideneamino-N-methyl carbamate is dissolved in 100 ml of tetrahydrofuran and 50 ml of benzene. To this solution there are added 15.8 g of pyridine and then dropwise, at 0° to 5° C, 13.5 g of $S_2Cl_2$; the reaction mixture is stirred at this temperature for 10 hours and subsequently filtered with suction. The residue is washed on the suction filter with water, dried, and recrystallised from methyl-ethyl ketone. There are obtained colourless crystals of the compound of the formula

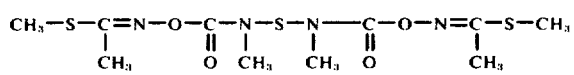

having a melting point of 169° – 170° C.

The following compounds are obtained in an analogous manner:
a. bis-[0-(1-ethylthioethylimino)-N-methylcarbamic acid]-N,N'-sulphide; m.p. 136°–139° C;
b. bis-[0-(1-n-pentylthioethylimino)-N-methylcarbamic acid]-N,N'-sulphide; m. p. 117°–119° C.

EXAMPLE 2

Insecticidal stomach poison action

Cotton plants were sprayed with a 0.05% aqueous active-substance emulsion (obtained from a 10% emulsifiable concentrate).

After the drying of the resulting coating, Spodoptera littoralis or Heliothis virescens larvae $L_3$ were placed on the cotton plants.

The test was carried out at 24° C with 60° relative humidity.

Compounds according to Example 1 exhibited in the above test a good insecticidal stomach poison action against Spodoptera littoralis and Heliothis virescens larvae.

EXAMPLE 3

Insecticidal contact action

One day before application of the active substance, broad beans (*Vicia fabae*) grown in pots were infested with about 200 bean aphids (*Aphis fabae*) per plant. The spray solution of the active substance was applied by means of a compressed-air sprayer to the leaves infested with bean aphids. The test solutions (spray solution) were prepared from a 25% wettable powder of the test preparations, and were applied in concentrations of 1000 ppm, 100 ppm, 10 ppm and 1 ppm to the test plants. An evaluation was made 24 hours after application.

The compounds according to Example 1 exhibited in the above test a good insecticidal contact action against *Aphis fabae*.

I claim:
1. A compound of formula 1

wherein R represents a $C_1$-$C_5$-alkyl radical.

2. A compound according to claim 1 wherein

R represents a methyl, ethyl, n-propyl, isopropyl, n-butyl or i-butyl radical.

3. Bis-[O-(1-methylthioethylimino)-N-methyl-carbamic acid]-N,N'-sulphide according to claim 2.

4. Bis-[O-(1-ethylthioethylimino)-N-methyl-carbamic acid]-N,N'-sulphide according to claim 2.

5. An insecticidal composition comprising an insecticidally effective amount of a compound according to claim 1, together with a suitable carrier therefor.

6. The composition of claim 5, wherein in said compound R represents a methyl, ethyl, n-propyl, isopropyl, n-butyl or i-butyl radical.

7. The composition of claim 6, wherein said compound is bis-[O-(1-methylthioethylimino)-N-methyl-carbamic acid]-N,N'-sulphide.

8. The composition of claim 6, wherein said compound is bis-[O-(1-ethylthioethylimino)-N-methyl-carbamic acid]-N,N'-sulphide.

9. A method for combatting insects which comprises applying to the locus of said insects an insecticidally effective amount of a compound according to claim 1.

10. The method of claim 9, wherein said locus is cotton plants.

11. The method of claim 9, wherein in said compound R represents a methyl, ethyl, n-propyl, isopropyl, n-butyl or i-butyl radical.

12. The method of claim 11, wherein said compound is bis-[O-(1-methylthioethylimino)-N-methyl-carbamic acid]-N,N'-sulphide.

13. The method of claim 11, wherein said compound is bis-[O-(1-ethylthioethylimino)-N-methyl-carbamic acid]-N,N'-sulphide.

* * * * *

Notice of Adverse Decision in Interference

In Interference No. 99,758, involving Patent No. 4,004,031, J. Drabek, BIS-(0-1-ALKYLTHIO-ETHYLIMINO)-N-METHYL-CARBAMIC ACID)-N,N'-SULPHIDE INSECTICIDES, final judgment adverse to the patentee was rendered Aug. 20, 1981, as to claims 1–3, 5–7 and 9–12.

[*Official Gazette Feb. 1, 1983.*]